(12) United States Patent
Bottiger et al.

(10) Patent No.: US 9,097,624 B1
(45) Date of Patent: Aug. 4, 2015

(54) EXTERNAL FILTER ASSEMBLY ADAPTED FOR MODIFYING A SUCTION CLEANING DEVICE TO PERFORM BIOLOGICAL SAMPLING

(71) Applicant: U.S. Army Research Development and Engineering Command, Washington, DC (US)

(72) Inventors: Jerold R. Bottiger, Aberdeen, MD (US); Jana S. Kesavan, Catonsville, MD (US)

(73) Assignee: The United States of America as Represented by the Secretary of the Army, Washington, DC (US)

( * ) Notice: Subject to any disclaimer, the term of this patent is extended or adjusted under 35 U.S.C. 154(b) by 47 days.

(21) Appl. No.: 13/782,344

(22) Filed: Mar. 1, 2013

(51) Int. Cl.
  *G01N 1/24* (2006.01)
  *G01N 1/22* (2006.01)
  *A47L 7/00* (2006.01)
  *A47L 9/12* (2006.01)

(52) U.S. Cl.
  CPC ... *G01N 1/24* (2013.01); *A47L 7/00* (2013.01); *A47L 9/12* (2013.01); *G01N 1/2205* (2013.01)

(58) Field of Classification Search
  CPC ........ B01D 46/02; B24B 21/04; B24B 55/06; A47L 7/00; A47L 9/12; G01N 1/24; G01N 1/2205
  USPC ................ 55/385.1, 471, 472, 473, 439, 422; 73/863.11, 28.01, 863.12, 863.21, 73/863.23; 422/186.07, 186.1; 15/344, 15/347
  See application file for complete search history.

(56) References Cited

U.S. PATENT DOCUMENTS

| | | | |
|---|---|---|---|
| 3,760,538 A * | 9/1973 | Solheim | 451/297 |
| 4,613,348 A * | 9/1986 | Natale | 55/318 |
| 5,047,075 A * | 9/1991 | Lin | 55/382 |
| 5,069,696 A * | 12/1991 | Bruno, III | 55/476 |
| 5,490,336 A * | 2/1996 | Smick et al. | 34/97 |
| 5,702,493 A * | 12/1997 | Everetts et al. | 55/356 |
| 5,840,091 A * | 11/1998 | Strong | 55/385.1 |
| 6,517,560 B1 * | 2/2003 | Toth et al. | 606/171 |
| 6,524,361 B1 * | 2/2003 | Thornton et al. | 55/385.4 |
| 7,122,065 B2 * | 10/2006 | Fox | 55/306 |
| 7,407,530 B2 * | 8/2008 | Chen | 95/147 |
| 7,588,730 B2 * | 9/2009 | Buechler et al. | 422/534 |
| 7,628,834 B2 * | 12/2009 | Huang et al. | 55/385.1 |
| 8,069,529 B2 * | 12/2011 | Groff et al. | 15/344 |
| 2004/0093756 A1 * | 5/2004 | Carlucci et al. | 34/82 |
| 2006/0182672 A1 * | 8/2006 | Hallam | 422/186.07 |
| 2007/0245699 A1 * | 10/2007 | Landman et al. | 55/385.1 |
| 2008/0148697 A1 * | 6/2008 | Liang et al. | 55/482 |
| 2009/0038277 A1 * | 2/2009 | Huang | 55/385.1 |
| 2010/0115898 A1 * | 5/2010 | Whittemore | 55/504 |
| 2014/0075712 A1 * | 3/2014 | Robertson et al. | 15/344 |

* cited by examiner

*Primary Examiner* — Duane Smith
*Assistant Examiner* — Minh-Chau Pham
(74) *Attorney, Agent, or Firm* — Ulysses John Biffoni

(57) ABSTRACT

An external filter assembly adapted for modifying a suction cleaning device to sample relatively small particles from various surfaces and/or the ambient air, includes a housing having a first open end, a second open end and a throughbore between the first and second open ends, a filter adapted for capturing particles with particle sizes greater than 0.1 micrometer, the filter being mounted on and enclosing the first open end, and means for securely retaining the second open end of the housing on an exhaust port of the suction cleaning device in communication with the housing throughbore.

12 Claims, 3 Drawing Sheets

EXTERNAL FILTER ASSEMBLY ADAPTED FOR MODIFYING A SUCTION CLEANING DEVICE TO PERFORM BIOLOGICAL SAMPLING

GOVERNMENT INTEREST

The invention described herein may be manufactured, used and licensed by or for the U.S. Government.

FIELD OF THE INVENTION

The present invention relates to biological sampling and collection, and more particularly to an external filter assembly adapted for modifying a suction cleaning device to sample relatively small particles from various hard to sample surfaces such as carpets, cloth chairs, tree leaves, and grass and/or the ambient air for subsequent biological testing and analysis.

BACKGROUND OF THE INVENTION

Sampling devices have been used extensively to identify microbes and other bioagents for various applications including protection of military and civilian population against enemy attacks. Such sampling devices are typically designed to selectively sample either air or surfaces. Aerosol samplers include pre-collectors and a number of concentration stages for isolating the particle sizes of interest. Thus, these aerosol sampling devices are heavy and require high power for operation. Surface sampling devices contain components for managing liquids, and are thus difficult to operate in a dynamic environment and not readily portable. In addition, surface sampling devices are typically incapable of separating the sample particles by size, resulting in samples containing undesirable larger size particles which undesirably interfere with analysis of any bioagents in the sample. These sampling devices are not readily portable, not suited for large area sampling, and require alternating current power sources.

Other sampling devices selected from Q-tips, sponges and swabs to sample surfaces visibly tainted with powder are available. However, methods using such devices are only suitable for non-porous surfaces and small area sampling, thus they are tedious, time consuming and labor intensive to implement.

Accordingly, there is a need in the art to develop an external filter assembly designed to convert a suction cleaning device such as a portable, hand-holdable vacuum cleaner into a sampling device, thus enabling large numbers of sampling devices to be rapidly constructed using commercially available components in short time and at relatively modest cost. There is a further need for an external filter assembly adapted for modifying a suction cleaning device to perform biological sampling in a manner to enhance portability and sampling area size, and reduce cost, while producing a testable quantity of aerosol and/or surface-based particles for subsequent testing and analysis.

SUMMARY OF THE INVENTION

The present invention relates generally to an external filter assembly adapted for modifying a suction cleaning device such as a vacuum cleaner to sample relatively small particles from various surfaces and/or the ambient air for subsequent biological testing and analysis. The filter assembly of the present invention is designed with enhanced flexibility for accommodating different suction cleaning device configurations. In this manner, the present invention can be used to rapidly construct a large number of sampling devices using commercially available components in a relatively short period of time and at a relatively modest cost. The filter assembly of the present invention produces a sampling device that is portable and has a large area of sampling coverage. The filter assembly of the present invention is relatively simple and cost effective to make and implement.

Generally, the suction cleaning device is adapted to vacuum and capture particulates having sizes of 10 micrometers and greater. When properly installed on the suction cleaning device, the filter assembly of the present invention is designed to capture any remaining particles missed by the suction cleaning device with a minimum collection efficiency of 50% for 0.3 to 0.4 micrometer and collection efficiency of 80% or better for 1.0 micrometer or larger after they exit the exhaust port of the suction cleaning device. Particles passing out of the suction cleaning device are generally of interest for biological testing and analysis. In this manner, the present invention enables the separation of the relatively large size particulates (e.g., hair, fur, dust and other debris) from the smaller size particles such as spores, bacterium, viruses, and the like, thereby effectively isolating the small particles for testing and analysis.

In one aspect of the present invention, there is provided an external filter assembly adapted for modifying a suction cleaning device to sample relatively small particles, comprising:

a housing having a first open end, a second open end and a throughbore between the first and second open ends;

a filter adapted for capturing particles with particle sizes of greater than 0.1 micrometer, the filter being mounted on and enclosing the first open end; and means for securely retaining the second open end of the housing on an exhaust port of the suction cleaning device in communication with the housing throughbore.

In further aspect of the present invention, there is provided a sampling device for sampling relatively small particles from air and/or surfaces, including:

a portable, hand-holdable suction cleaning device having an exhaust port, the suction cleaning device adapted for capturing particulates with sizes of greater than 10 micrometers; and an external filter assembly described above securely affixed to the exhaust port of the suction cleaning device with the second open end of the filter assembly fluidly coupled to the exhaust port whereby the exhaust port and throughbore of the filter assembly are in communication.

In another aspect of the present invention, there is provided a method for modifying a suction cleaning device to sample relatively small particles, including the steps of:

acquiring a filter assembly described above; and mounting the second open end of the filter assembly to an external exhaust port of the suction cleaning device in communication with the housing throughbore of the filter assembly.

BRIEF DESCRIPTION OF THE DRAWINGS

The following drawings are illustrative of embodiments of the invention and are not intended to limit the invention as encompassed by the claims forming part of the invention, wherein like items are identified by the same reference designation.

DETAILED DESCRIPTION OF THE INVENTION

The present invention is directed to an external filter assembly adapted for modifying a suction cleaning device such as a vacuum cleaner to sample relatively small particles from various surfaces and/or the ambient air for subsequent biological testing and analysis. The filter assembly of the present invention is flexible to accommodate different suction cleaning device configurations. The present invention can be used to rapidly construct a large number of sampling devices using commercially available components in a relatively short period of time and at a relatively modest cost. The filter assembly of the present invention facilitates construction of a portable sampling device capable of providing a large area of sampling coverage. The filter assembly of the present invention is relatively simple and cost effective to make and implement. It also allows for sampling from hard to sample surfaces such as carpets, cloth chairs, tree leaves and grass.

Generally, the suction cleaning device is adapted to vacuum and capture particulates 10 micrometers or larger. When properly installed on the suction cleaning device, the filter assembly of the present invention is designed to capture any remaining particles missed by the suction cleaning device with a minimum collection efficiency of 50% for 0.3 to 0.4 micrometer or a minimum collection efficiency of 80% or better for 1.0 micrometer or larger after they exit the exhaust port of the suction cleaning device. Particles passing out of the suction cleaning device are generally of interest for biological testing and analysis. In this manner, the present invention enables the separation of the relatively large size particulates (e.g., hair, fur, dust and other debris) from the smaller size particles such as spores, bacterium, viruses, and the like, thereby effectively isolating the small particles for testing and analysis.

There is provided an external filter assembly adapted for modifying a conventional suction cleaning device to sample relatively small particles from various surfaces and/or the ambient air including a housing having a first open end, a second open end and a throughbore between the first and second open ends, a filter adapted for capturing particles with particle sizes of greater than 0.1 micrometer, the filter being mounted on and enclosing the first open end and means for sec rely retaining the second open end of the housing on an exhaust port of the suction cleaning device in communication with the housing throughbore.

Figure 1:
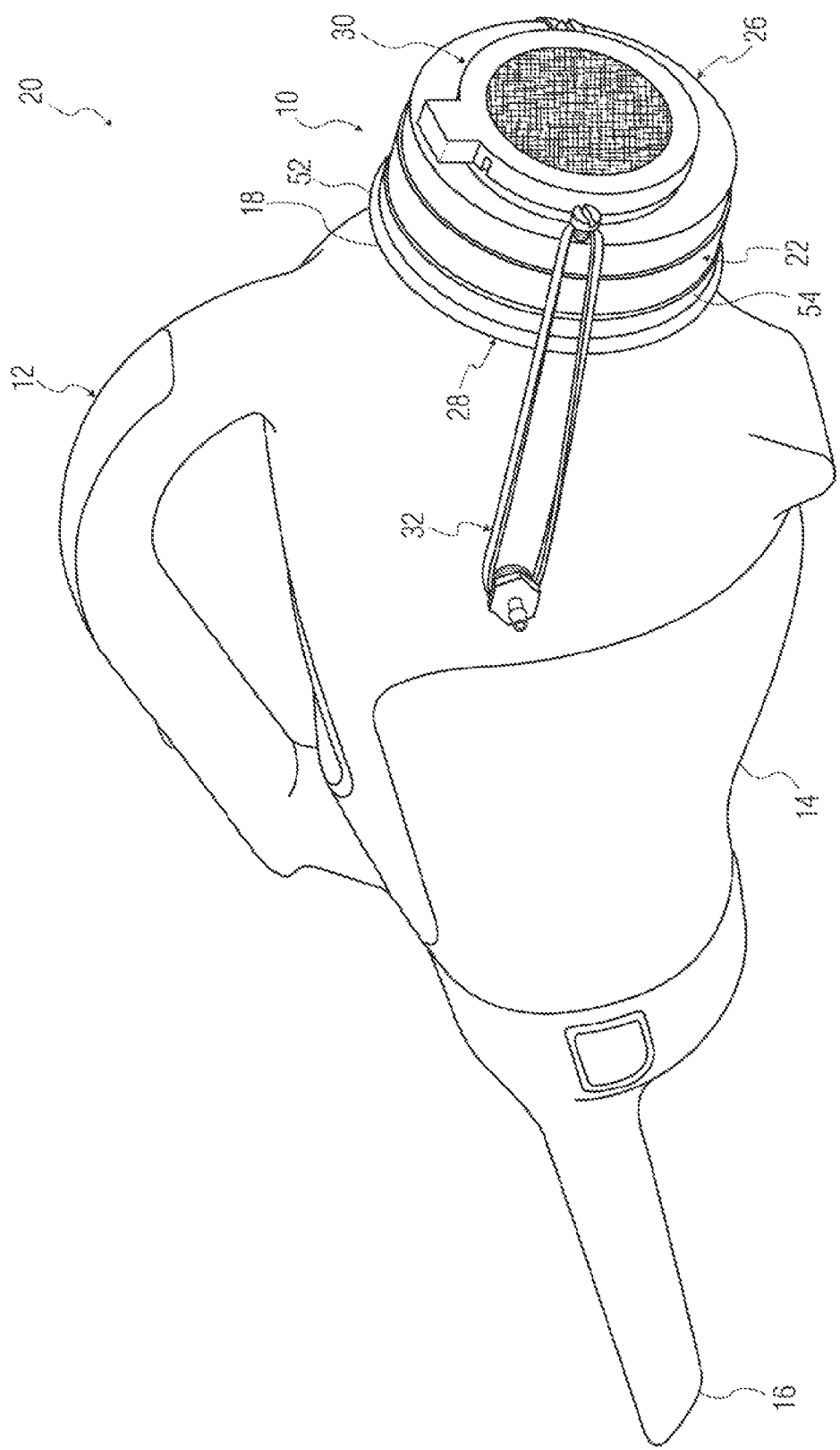
FIG. 1 is a perspective view of an external filter assembly modifying a suction device to provide a sampling device for sampling relatively small particles from various surfaces and/or the ambient air for one embodiment of the present invention.

Referring to FIG. 1, an external filter assembly identified generally by reference numeral 10 is useful for modifying a suction cleaning device 12 to sample relatively small particles from various surfaces and/or the ambient air in accordance with one embodiment of the present invention. The suction cleaning device 12 generally includes a casing 14 housing a motor driven air pump (not shown) in communication with an intake nozzle 16 and an exhaust port 18, and a non-HEPA porous vacuum filter (not shown) typically in the form of a fiber or foam pouch housed in a debris holding canister within the casing 14. The air pump not shown) creates a pressure drop at the intake nozzle 16, thereby drawing ambient air and debris including particulates and particles outside the cleaning device 12 into and through the intake nozzle 16 in a constant air stream through the air pump (not shown) and out the exhaust port 18.

The non-HERA, porous vacuum filter (not shown) positioned in the path of air stream before the exhaust port 18, captures relatively large particulates (e.g., debris, hair, fur, dirt, soil, sand and the like), which are typically 10 micrometers or larger, and allows the air stream to pass therethrough exiting the exhaust port 18. The suction cleaning device 12 can be selected from a hand-holdable portable vacuum cleaner, preferably cordless, such as, for example, 14.4V DUSTBUSTER® Cordless Hand Vac vacuum cleaner Model No. CHV1410 available from Black & Decker Corporation of Towson, Md.

The filter assembly 10 is adapted for mounting on the vacuum exhaust port 18 of the cleaning device 12. Once mounted, the cleaning device 12 is modified into an air/surface sampling device 20 for sampling relatively small particles from the ambient air and/or surfaces. The sampling device 20 is especially suitable for collecting biological samples, which can be processed for biological testing and analysis. The filter assembly includes a tubular housing 22, a proximal end 24, a distal end 26, a gasket 28 located at the proximal end 24, a disc-shaped sample filter collector 30 affixed to the distal end 26: and a retaining mechanism 32 for securing the filter assembly 10 to the cleaning device 12. The sample filter collector 30 is adapted for capturing particles with particle sizes of greater than 0.1 micrometer, and preferably greater than 6.61 micrometer.

The housing 22 is constructed from any suitable rigid material such as, for example, glass, metal, wood, and polymer-based materials. The polymer-based material can be selected from plastics such as polycarbonates and acrylics. In one embodiment of the present invention, the housing 22 is composed of an optically transmissive material encompassing transparent and translucent materials. The housing 22 comprises a cylindrical shape having a diametric size suitable for accommodating the exhaust port 18 of the cleaning device 12. It will be understood that the size, shape and configuration of the housing 22 is not limited to the embodiment shown and described herein, and can encompass any size, shape and configuration necessary for mounting to the exhaust portal of a suction cleaning device.

The proximal end 24 of the filter assembly housing 22 is adapted for mounting over and enclosing the exhaust port 18 of the cleaning device 12, to receive the air stream exiting therefrom and to direct it through the sample filter collector 30. The filter media 48 of the sample filter collector 30 (see FIG. 2) captures any remaining particles in the air stream exiting from the cleaning device 12. Thus, the captured particles in the filter media 48 are generally in the range of from about 0.1 micrometer to 10 micrometers.

Figure 2:
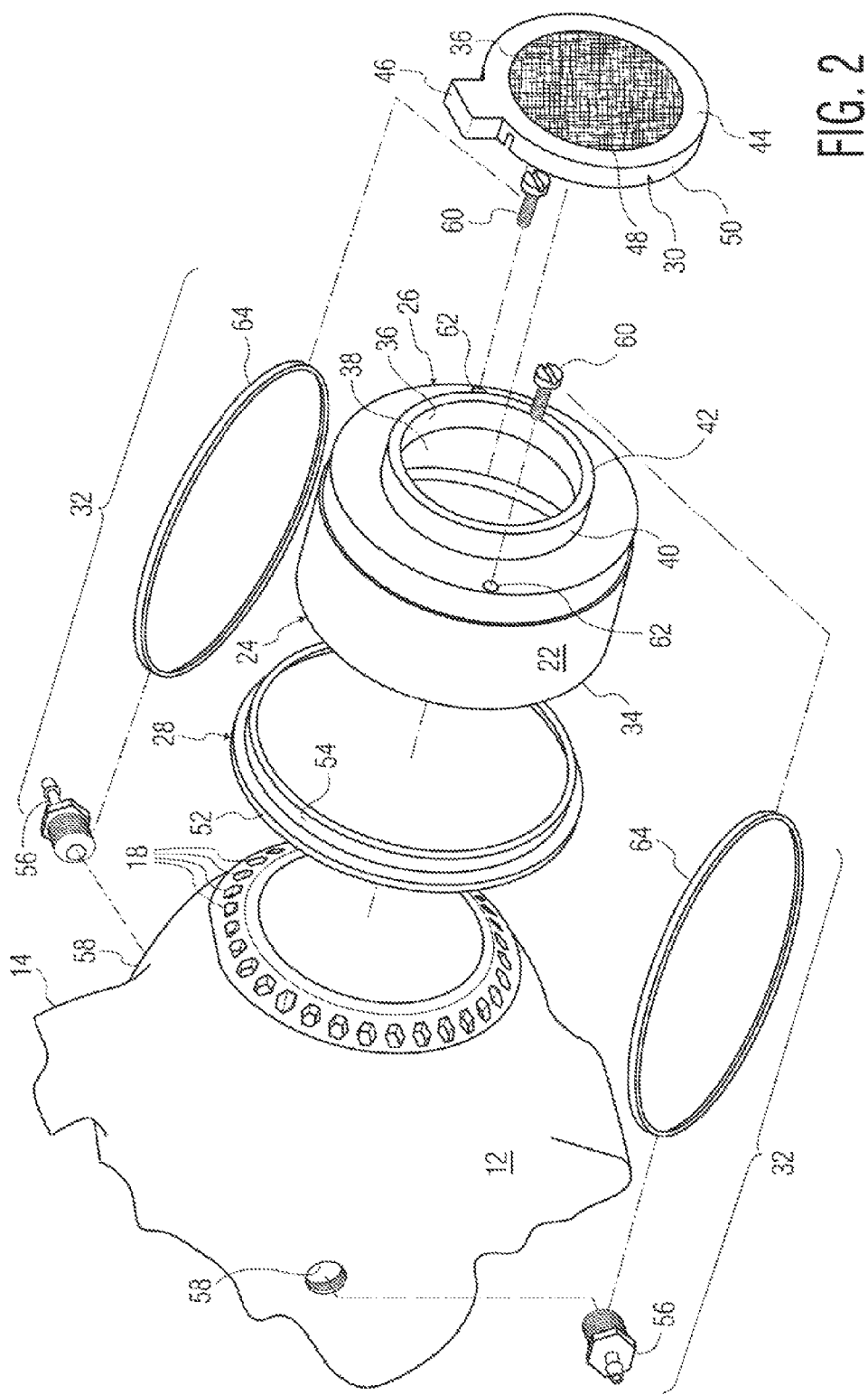
FIG. 2 is an exploded assembly view of the external filter assembly of FIG. 1 mounted on a suction device in accordance with the present invention.
Figure 3:
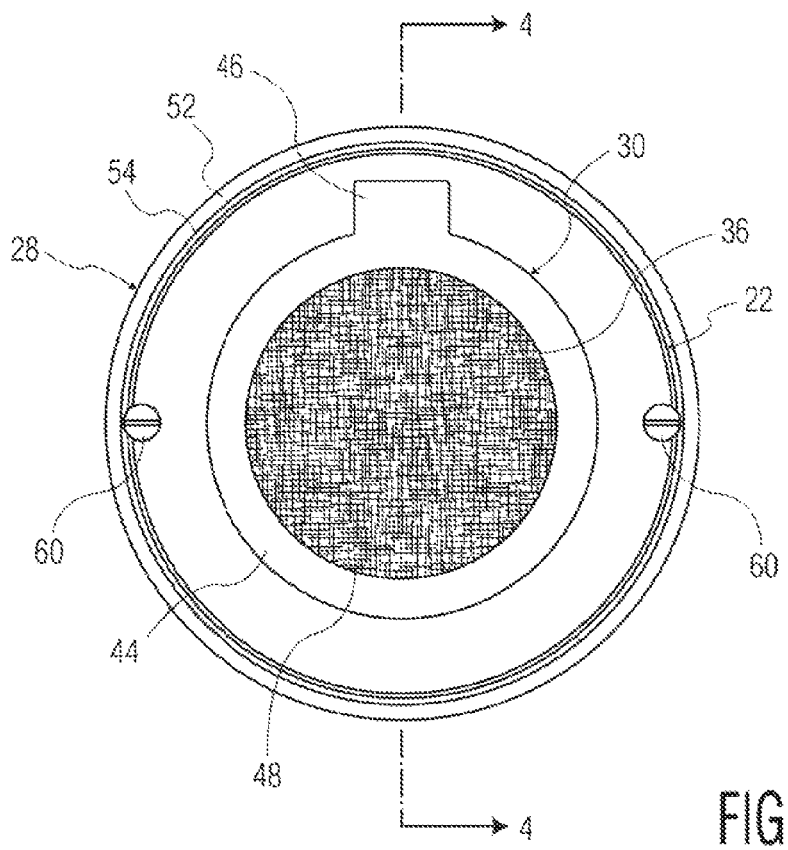
FIG. 3 is a front elevational view of the external filter assembly in accordance with the present invention.
Figure 4:
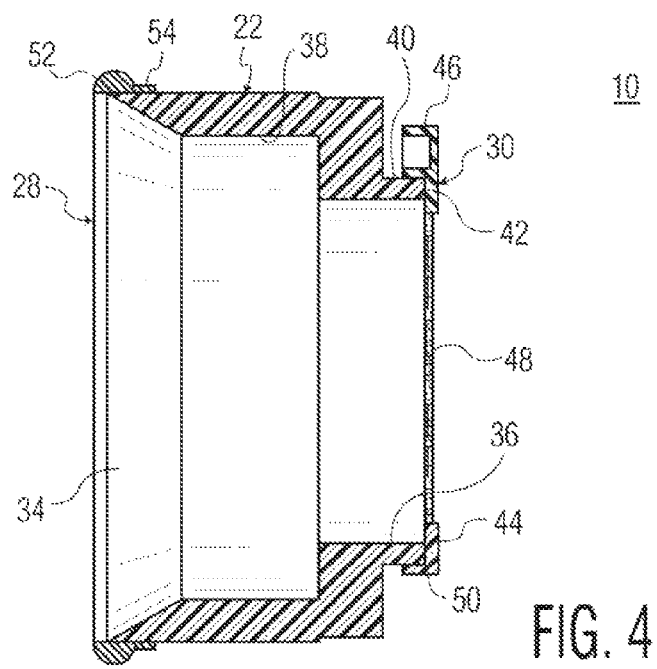
FIG. 4 is a side cross sectional view of the external filter assembly along lines 4-4 of FIG. 3 in accordance with the present invention.

Referring to FIGS. 2 through 4, particularly for filter assembly 10, the housing 22 includes an exhaust port opening 34 at the proximal end 24, a filter collector opening 36 at the distal end 26, and a throughbore 38 extending therebetween. The filter collector opening 36 a circular wall 40 with a top surface or edge 42 projecting from the distal end 26 of the housing 22. The sample filter collector 30 includes an opening 36 surrounded by a frame 44 with an outwardly extending tab 46, for retaining a centrally-located filter media 48, and a skirt 50 extending peripherally along the outer edge of the frame 44. The frame 44 and the skirt 50 are configured for frictional press fitting over the circular wall 40 of the filter collector opening 36. The filter media 48 is securely held in position by suitable means over the opening 36 of the housing 22.

The tab 46 provides a gripping surface portion for the user to remove and replace the sample filter collector 30 during use. The filter media 48 is configured to capture submicron size particles including biological pathogens, pathogenic bacteria, and spores. The filter media 48 is selected from an air filter material such as, for example, fiberglass, cellulose, microfibrous materials, and the like, suitable for removing or capturing at least 85% of all particles greater than 0.1 micrometer, and preferably at least 99.97% of all particles greater than 0.1 micrometer. In a preferred embodiment of the present invention, the filter media 48 is an electret filter media such as the type manufactured and/or sold by Research International Inc. of Monroe, Wash.

The proximal end 24 of the housing 22 is mounted over the exhaust port 18 in contact with the cleaning device casing 14 via a gasket 28. The gasket 28 ensures a seal tight engagement between the housing 22 and the cleaning device casing 14. Gasket 28 includes a circular base portion 52 and a peripheral wall 54 extending therealong. The peripheral wall 54 of the gasket 28 is configured for placement around the exhaust port opening 34 of the housing 22 for a snug fit retainment thereon, as shown. When the housing 22 of the filter assembly 10 is mounted over the exhaust port 18 of the cleaning device 12, the gasket base portion 52 maintains a tight sealing contact between the gasket 28 and the cleaning device casing 14.

The retaining mechanism 32 securely holds the proximal end 24 of the housing 22 to the exhaust port 18 of the cleaning device 12 in communication with the housing throughbore 38. The retaining mechanism 32 includes a pair of casing studs 56 threadedly engaged to corresponding openings 58 on the cleaning device casing 14, a pair of housing studs 60 threadedly engaged to corresponding openings 62, and a pair of elongated elastic band members 64 resiliently engaged and securely attached between respective studs 56 and 60 to securely hold the filter assembly 10 onto the cleaning device 12 to thereby provide the resulting sampling device 20.

It is noted that the filter assembly 10 of the present invention can be used to capture larger sample particles by removing the standard vacuum filter (not shown) from the suction cleaning device 12. In this configuration, the sampling device 20 can collect samples from hard to sample surfaces without utilizing size separation.

The present invention is also directed to a method for modifying a suction cleaning device to sample relatively small particles from various surfaces and/or the ambient air, which includes the steps of acquiring a filter assembly 10, and mounting the proximal end 24 of the filter assembly to an external exhaust port 18 of the suction cleaning device 12 in communication with the housing throughbore 38 of the filter assembly 10.

Example

Testing of Sampling Device of the Present Invention

Testing was conducted in an aerosol test chamber to determine the sampling efficiency of the sampling device of the present invention. *Bacillus atrophaeus* spores were aerolized into the chamber using a sonic nozzle and the aerosol was mixed with fans to achieve a uniform aerosol concentration in the chamber. The sampling device used was a Black & Decker DUSTBUSTER® vacuum cleaner equipped with the filter assembly 10 having a standard reference filter sampler 30. This is an electrets filter (standard filter cartridge assembly—part number 7100-134-232-01, Research International Inc., Monroe, Wash.) containing fibers with permanent static charge. These charges induce a charge in the aerosol passing through them and provide a capture mechanism for these aerosols. The sampling device sampled the air for about 3 minutes. The filters 48 were removed from the sample filter collector 30 for analysis.

The filters 48 were placed into 20 mL of PBST with 0.01% Triton X and were shaken on a Table Shaker (VWR VX2500 Multi-tube Vortexer) for about 10 minutes. Samples (100 microliters) were plated, on agar plates in triplicate and incubated overnight. The colonies were counted the next day and the sampling efficiency was determined based on airflow rate and colony count.

The results showed that the air flow through the filter was approximately 585 liters per minute with all the air directed through it, and the sampling efficiency was about 23%. This is an acceptable number considering the larger particles which could adversely affect the analysis have been removed thereby allowing sampling of larger areas for each filter.

This device was also used in sampling bacteria in field testing. Samples were taken from grass, concrete floor, and other surfaces, and the results showed significant amounts of bacteria collected by the sampling device.

The forgoing discussion discloses and describes merely exemplary embodiments of the present invention. One skilled in the art will readily recognize from such discussion, and from the accompanying claims, that various changes, modifications, and variations can be made therein without departing from the spirit and scope of the invention as defined in the following claims.

What is claimed is:

1. A collection and sampling, device for sampling particles from air and/or surfaces, comprising:
   a portable hand-holdable suction cleaning device having an exhaust port and in intake nozzle adapted for collecting samples from surfaces, said suction cleaning device including a filter adapted for capturing particles with sizes of greater than 10 micrometers; and
   an external filter assembly securely affixed to the exhaust port of said portable, hand-holdable suction cleaning device, said external filter assembly comprising:
   a housing having a proximal open end, a distal open end and a throughbore between said proximal and distal open ends;
   a filter element adapted for capturing particles with particle sizes of greater than 0.01 micrometer, said filter element being mounted on and enclosing the distal open end of said housing; and
   means for securely retaining the proximal open end of said housing on said exhaust port of said suction cleaning device so that the proximal end of the external filter assembly housing is fluidly coupled to the exhaust port whereby the exhaust port and throughbore of the filter assembly housing are in fluid communication.

2. The filter assembly of claim 1, wherein the housing is composed of an optically transmissive material.

3. The filter assembly of claim 1, wherein the housing is composed of material.

4. The filter assembly of claim 3, wherein the housing is composed of plastic acrylic.

5. The filter assembly of claim 1, wherein the filter element includes an electret filter media.

6. The filter assembly of claim 1, wherein the retaining means comprises:
   a first pair of studs, each positioned on opposed portions of the suction cleaning device;

a second pair of studs, each positioned on opposed portions of the housing; and a pair of elongate members, each securely attached between corresponding one of said first pair of studs and one of said second pair of studs, for securely retaining said second end of said housing on the exhaust port of said suction cleaning device.

7. The filter assembly of claim 1, further comprising a gasket extending along the periphery of the proximal open end of the housing.

8. The filter assembly of claim 1, wherein the filter element is removable.

9. The filter assembly of claim 1, wherein the litter element is disc-shaped.

10. The filter assembly of claim 1, wherein the filter element further includes an outwardly and radially-projecting tab.

11. The filter assembly of claim 1, wherein the filter element includes a filter media adapted for capturing particles with sizes greater than 0.01 micrometer.

12. A method for modifying a suction cleaning device to sample particles from various surfaces and/or the ambient air, comprising the steps of:

acquiring a filter assembly of claim 1; and mounting the proximal open end of the filter assembly to an external exhaust port of the suction cleaning device in communication with said housing throughbore of the filter assembly.

\* \* \* \* \*